US00PP09949P

United States Patent [19]

VandenBerg

[11] Patent Number: Plant 9,949

[45] Date of Patent: Jul. 8, 1997

[54] CHRYSANTHEMUM PLANT NAMED 'REGAL VOLARE'

[75] Inventor: Cornelis P. VandenBerg, Salinas, Calif.

[73] Assignee: Yoder Brothers, Inc., Barberton, Ohio

[21] Appl. No.: 617,184

[22] Filed: Mar. 18, 1996

[51] Int. Cl.[6] ..... A01H 5/00

[52] U.S. Cl. ..... Plt./74.1

[58] Field of Search ..... Plt./74.1, 82.4

[56] References Cited

U.S. PATENT DOCUMENTS

| | | | |
|---|---|---|---|
| P.P. 8,808 | 6/1994 | VandenBerg | Plt./82.4 |
| P.P. 8,829 | 7/1994 | VandenBerg | Plt./74.1 |
| P.P. 9,423 | 1/1996 | VandenBerg | Plt./82.4 |
| 4,616,099 | 10/1986 | Sparkes | 47/58 |

OTHER PUBLICATIONS

Broertjes, et al., 1980, "A mutant of a mutant of a . . . Irradiation of progressive radiation-induced mutants in a mutation breeding programme with *Chrysanthemum morifolium*", Euphytica, 29:525–530.

Gasling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by x-rays", Am. Soc. Hort. Sci. Proc., pp. 613–620.

Broertjes, 1966, "Mutation breeding of chrysanthemums", Euphytica, 15:156–162.

Dowrick, et al., 1966, "The induction of mutations in chrysanthemum using x- and gamma radiation", Euphytica, 15:204–210.

*Primary Examiner*—Howard J. Locker

*Attorney, Agent, or Firm*—C. A. Whealy

[57] ABSTRACT

A distinct cultivar of Chrysanthemum plant named Regal Volare, characterized by its flat capitulum form; medium to large daisy-type inflorescences; attractive dark pink ray florets and yellow disc florets; numerous inflorescences per plant; and good postproduction longevity.

2 Drawing Sheets

The present invention relates to a new and distinct cultivar of Chrysanthemum plant, botanically known as *Dendranthema grandiflora* and referred to by the cultivar name Regal Volare.

The new cultivar is a product of a mutation induction breeding program conducted by the inventor in Salinas, Calif. The objective of the mutation induction breeding program is to create new Chrysanthemum cultivars having desirable inflorescence and foliage colors and inflorescences and foliage with good form and substance.

The new cultivar originated by exposing 75 unrooted cuttings of the Chrysanthemum selection Dark Volare (not patented) to an X-ray radiation level of 2,000 rads. Following the radiation treatment, the cuttings were rooted and terminal apices were removed (pinched) three times to promote lateral branch development. After lateral branches from the third pinch reached sufficient size, 255 terminal cuttings were harvested, planted and flowered in Salinas, Calif. The cultivar Regal Volare was discovered and selected by the inventor as a single flowering plant within this population. The selection of this plant was based on its desirable inflorescence color and form and good inflorescence and foliage substance.

Asexual reproduction of the new cultivar by terminal cuttings taken at Salinas, Calif. has shown tha the unique features of this new Chrysanthemum are stable and reproduced true to type in successive generations.

The following traits have been repeatedly observed and are determined to be the unique characteristics of Regal Volare. These characteristics in combination distinguish Regal Volare as a new and distinct cultivar:

1. Flat capitulum form.
2. Medium to large daisy-type inflorescences.
3. Attractive dark pink ray florets and yellow disc florets.
4. Numerous infloresences per plant.
5. Good postproduction longevity with inflorescences maintaining good substance and color for more than three weeks in an interior environment.

The cultivar Regal Volare has not been observed under all possible environmental conditions. The phenotype may vary somewhat with variations in environment such as temperature, daylength and light intensity, without, however, any variance in genotype.

The new Chrysanthemum is similar in plant havit to the mutation parent cultivar Dark Volare. However in side-by-side comparison in Salinas, Calif. under commercial practice, plants of the new Chrysanthemum have ray florets that are dark pink in color whereas ray florets of plants of Dark Volare are medium pink in color.

Plants of the cultivar Regal Volare are also similar to the cultivar Volare (disclosed in U.S. Plant Pat. No. 8,058). However, in side-by-side comparisons conducted in Salinas, Calif. under commercial practice, ray floret color on plants of the cultivar Regal Volare is dark pink (R.H.S. 70B) compared to the light pink (75D) ray floret color of the cultivar Volare. Additionally in these evaluations, the new Chrysanthemum differed from the cultivar Volare in the following characteristics.

1. Plants of the cultivar Regal Volare were approximately 5 cm shorter than plants of the cultivar Volare.
2. Plants of the cultivar Regal Volare flowered 2 to 3 days later than plants of the cultivar Volare.
3. Inflorescences of plants of the cultivar Regal Volare were smaller in diameter than inflorescences of the cultivar Volare.

In side-by-side comparisons conducted in Bogota, Colombia, under commercial practice, the new Chrysanthemum differed form the cultivar Volare in the following characteristics:

1. Plants of the cultivar Regal Volare were 5 to 7.5 cm shorter than plants of the cultivar Volare.
2. Plants of the cultivar Regal Volare flowered 2 to 5 days later than plants of the cultivar Volare.

3. No difference in inflorescence size between the two cultivars was observed.

The accompanying colored photographs illustrate the overall appearance of the new cultivar, showing the colors as true as it is reasonably possible to obtain in colored reproductions of this type.

The first photograph comprises a side perspective view of a typical flowering stem of Regal Volare grown as a single stem spray cut Chrysanthemum.

The second photograph comprises a top perspective view of the upper surface of leaves of the cultivar Regal Volare at six different stages of development showing the differences in size and lobation development.

In the following description, color references are made to The Royal Horticultural Society Colour Chart except where general terms of ordinary dictionary significance are used. The following observations and measurements describe plants grown in Salinas Calif., under commercial practice in a polyethylene-covered greenhouse with night temperatures ranging from 15 to 17 C., day temperatures up to 24 C., and light levels of 2,500 to 3,000 footcandles. After planting rooted cuttings of the new cultivar, plants received 11 long day/short nights following by short day/long nights until flowering. Measurements and numerical values represent averages for six typical flowering stems.

Botanical classification: *Dendranthema grandiflora* cultivar Regal Volare.

Commercial classification: Daisy spray-type cut chrysanthemum.

Parentage: Induced mutation of *Dendranthema grandiflora* cultivar Dark Volare (not patented).

Propagation:

*Type.*—Terminal tip cuttings.

*Time to rooting.*—7 to 10 days with soil temperatures of 21 C.

*Rooting habit.*—Fine, fibrous and well-branched.

Plant description:

*Appearance.*—Perennial herbaceous daisy spray-type cut flower. Stems upright, uniform habit and freely branching.

*Flowering stem length.*—80 to 85 cm.

*Foliage description.—Leaf arrangement: Alternate. Leaf size, fully expanded: Length: About* 10.5 cm. Width: About 6 cm. Leaf apex: Acuminate. Leaf base: Attenuate. Leaf margin: Palmately lobed. Leaf texture: Upper and under surfaces slightly pubescent. Veins prominent on under surface. Petiole length: About 2 cm. Color: Young foliage upper surface: 147A. Young foliage under surface: 147B. Mature foliage upper surface: 147A. Mature foliage under surface: 147B. Venation upper surface: 147B. Venation under surface: 147B. Petiole: 147A.

Flowering description:

*Appearance.*—Daisy inflorescence form. Inflorescences borne on terminals above foliage, arising from leaf axils. Disk and ray florets arranged acropetally on a flat capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to 1.5 to 2 weeks of long day/short night conditions after planting followed by photoinductive short day/long night conditions, flower about 55 to 57 days later.

*Postproduction longevity.*—In an interior environment, inflorescences of cut flowering stems will maintain good color and substance for at least three weeks in an interior environment.

*Quantity of inflorescences.*—8 to 12 inflorescences per flowering stem.

*Inflorescence size.*—Diameter: About 7 cm. Depth (height): About 1.2 cm. Diameter of disc: About 2 cm.

*Ray florets.*—Shape: Elongated, narrow. Size: Length: About 3.25 cm. Width: About 1.2 cm. Apex: Dentate. Base: Acute. Margin: Entire. Texture: Satiny, smooth, glabrous, ribbed lengthwise. Aspect: Flat. Number of ray florets per inflorescence: About 24. Color: When opening, upper surface: 70B. When opening, under surface: 70D. Mature, upper surface: 70B, color does not fade with further development. Mature, under surface: 70D, color does not fade with further development.

*Disc florets.*—Shape: Tubular. Size: Length: About 3 mm. Width: About 1 mm. Number of disc florets per inflorescence: About 220. Color: Immature: 144B/151B. Mature: 7A.

*Peduncle.*—Aspect: Strong and angled about 45° to the stem. Length: First peduncle: About 8.5 cm. Fourth peduncle: About 11.5 cm. Texture: Glabrous. Color: 147B.

*Reproductive organs.*—Androecium: Present on disc florets only. Anther color: 2B. Pollen: Moderate, 2B in color. Gynoecium: Present on both ray and disc florets.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named Regal Volare, as illustrated and described.

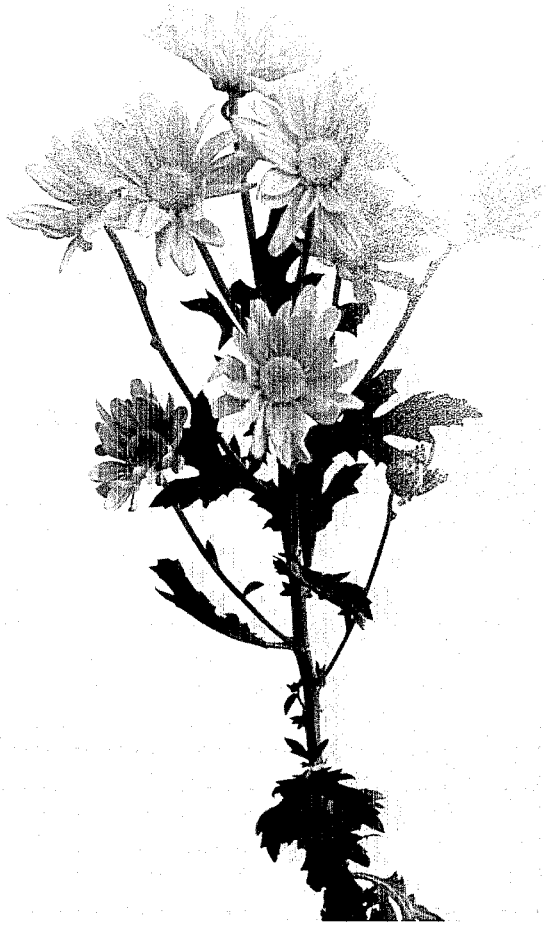

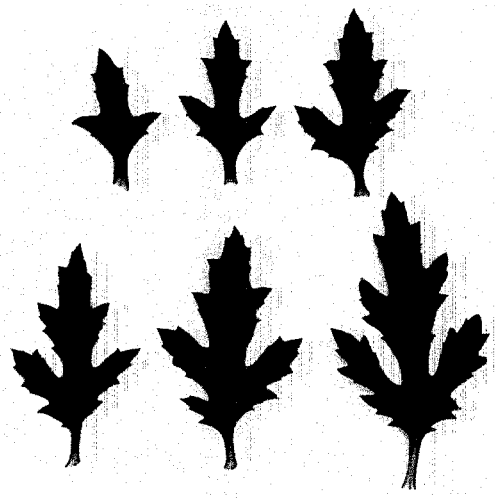

* * * * *